United States Patent
Loesel et al.

(10) Patent No.: US 8,088,124 B2
(45) Date of Patent: Jan. 3, 2012

(54) SYSTEM AND METHOD FOR PRECISE BEAM POSITIONING IN OCULAR SURGERY

(75) Inventors: Frieder Loesel, Mannheim (DE);
Mathias Glasmacher, Erlangen (DE);
Ulrich von Pape, Speyer (DE)

(73) Assignee: Technolas Perfect Vision GmbH, Munich (DE)

( * ) Notice: Subject to any disclaimer, the term of this patent is extended or adjusted under 35 U.S.C. 154(b) by 1245 days.

(21) Appl. No.: 11/625,213

(22) Filed: Jan. 19, 2007

(65) Prior Publication Data
US 2008/0177256 A1    Jul. 24, 2008

(51) Int. Cl.
*A61B 18/20* (2006.01)

(52) U.S. Cl. .............. 606/10; 606/4; 606/11; 351/205

(58) Field of Classification Search .............. 606/4–6, 606/10–12; 351/205–212; 607/88, 89; 128/898
See application file for complete search history.

(56) References Cited

U.S. PATENT DOCUMENTS

| | | | |
|---|---|---|---|
| 4,452,506 A | 6/1984 | Reeve et al. | |
| 4,474,423 A | 10/1984 | Bisbee et al. | |
| 4,812,641 A | 3/1989 | Ortiz, Jr. | |
| 4,838,631 A | 6/1989 | Chande et al. | |
| 5,098,426 A | 3/1992 | Sklar et al. | |
| 5,336,215 A * | 8/1994 | Hsueh et al. ................... | 606/4 |
| 5,493,109 A | 2/1996 | Wei et al. | |
| 5,620,436 A | 4/1997 | Lang et al. | |
| 6,004,314 A | 12/1999 | Wei et al. | |
| 6,091,074 A | 7/2000 | Korevaar | |
| 6,097,522 A | 8/2000 | Maerki et al. | |
| 6,322,556 B1 | 11/2001 | Gwon et al. | |
| 6,454,761 B1 | 9/2002 | Freedman | |
| 6,755,819 B1 * | 6/2004 | Waelti ............................. | 606/5 |
| 6,787,733 B2 | 9/2004 | Lubatschowski et al. | |
| 2004/0021874 A1 | 2/2004 | Shimmick | |
| 2005/0024586 A1 | 2/2005 | Teiwes et al. | |
| 2006/0187462 A1 * | 8/2006 | Srinivasan et al. ............ | 356/479 |
| 2006/0195076 A1 * | 8/2006 | Blumenkranz et al. .......... | 606/4 |
| 2007/0173794 A1 | 7/2007 | Frey et al. | |
| 2011/0202044 A1 | 8/2011 | Goldshleger et al. | |

FOREIGN PATENT DOCUMENTS
EP    1364632 A1    11/2003

OTHER PUBLICATIONS

NREL/TP-580-24190, A Look Back at the U.S. Department of Energy's Aquatic Species Program: Biodiesel from Algae, Jul. 1998.

* cited by examiner

*Primary Examiner* — Ahmed Farah
(74) *Attorney, Agent, or Firm* — Nydegger & Associates

(57) ABSTRACT

A system and method for ocular surgery includes a delivery system for generating and guiding a surgical laser beam to a focal point in a treatment area of an eye. Additionally, a contact device is employed for using the eye to establish a reference datum. Further, an optical detector is coupled to the beam path of the surgical laser to create a sequence of cross-sectional images. Each image visualizes both the reference datum and the focal point. Operationally, a computer then uses these images to position and move the focal point in the treatment area relative to the reference datum for surgery.

15 Claims, 1 Drawing Sheet

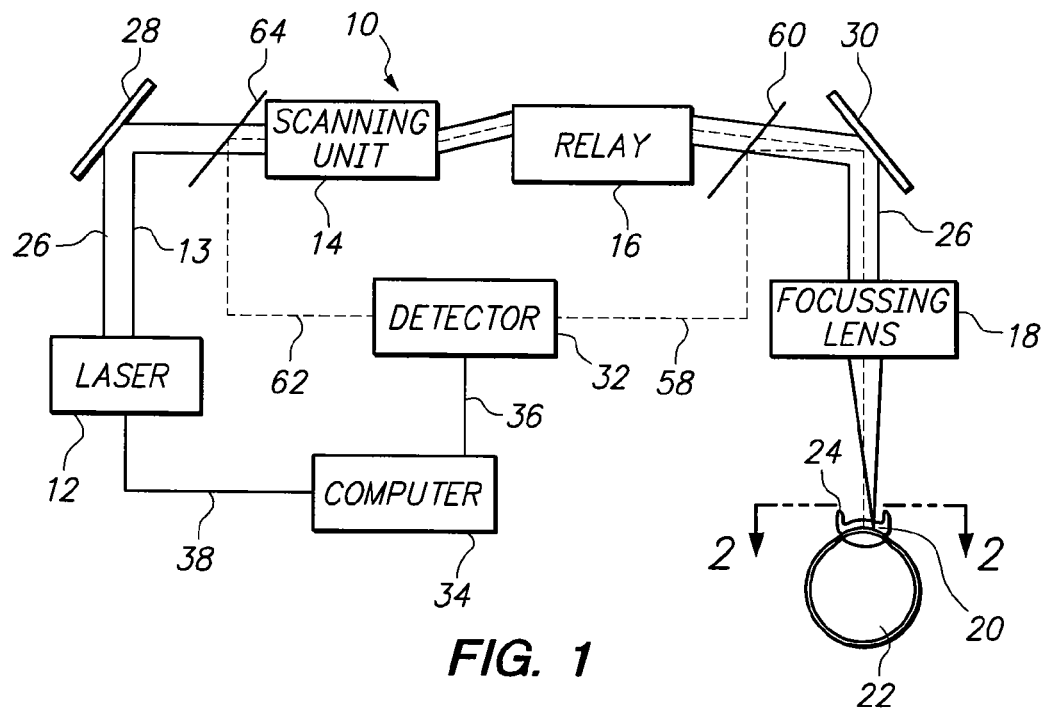
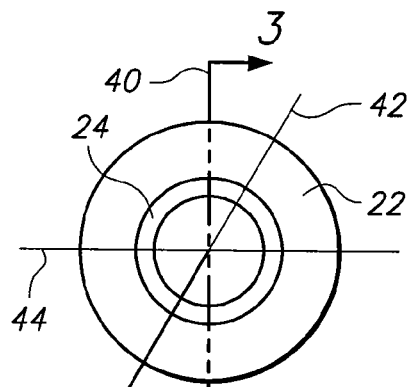
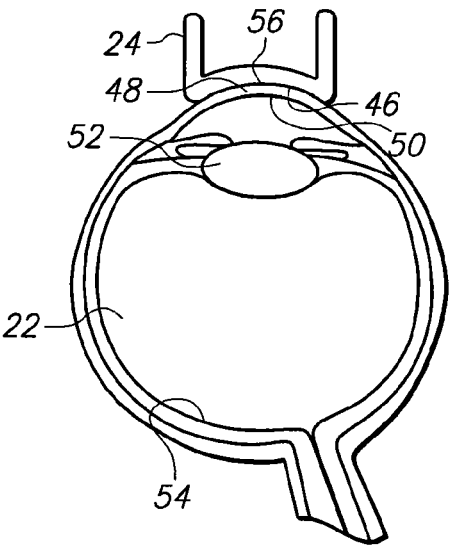
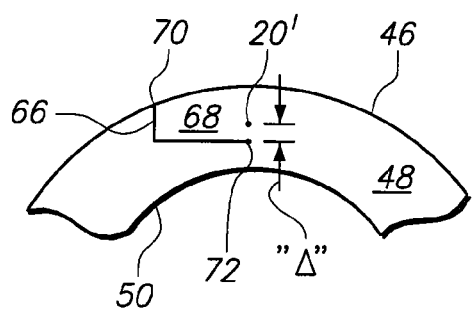
FIG. 1
FIG. 2
FIG. 3
FIG. 4

SYSTEM AND METHOD FOR PRECISE BEAM POSITIONING IN OCULAR SURGERY

FIELD OF THE INVENTION

The present invention pertains generally to systems and methods for performing ocular surgery. More particularly, the present invention pertains to computer-controlled laser surgical systems. The present invention is particularly, but not exclusively, useful as a system and a method that incorporate optical coherence tomography (OCT) techniques for the purpose of imaging both a treatment area and a reference datum, to control laser beam focal point movements within the treatment area during a surgical operation.

BACKGROUND OF THE INVENTION

When using a laser beam to perform ocular surgery, the precise movement of the laser beam's focal point through the tissue to be altered is absolutely imperative. Specifically, focal point position accuracies within about ten microns (10 μm) are preferable. To do this, the desired path for the laser beam's focal point must have a precisely defined start point. And, the laser beam's focal point must then be moved along the prescribed path. Although this can be accomplished in some situations with open loop control (i.e. having the laser beam focal point follow a pre-programmed path), in many other situations it may be more desirable to incorporate a closed loop feedback control system. Unlike open loop systems, closed loop feedback control systems provide continuous monitoring and corrections for deviations of the focal point. In either case, movements of the laser beam's focal point must be accomplished in the context of a reference datum.

An important requirement for any closed loop feedback control system is the need to accurately identify an appropriate error signal. As implied above, this error signal must be measurable. Thus, a reference datum is required from which the error signal can be measured. Once the error signal is identified, control of the system's performance is made by system adjustments that will nullify, or at least minimize, the error signal. Stated differently, deviations (i.e. error signals) from desired performance parameters must be determinable and maintained below an acceptable minimum. For the specific case involving feedback control of a surgical laser's focal point during ocular surgery, a reference datum that is anatomically related to the eye undergoing surgery needs to be selected. Further, knowledge of the location of the laser beam's focal point relative to the reference datum, and thus relative to a path through the eye, is also required.

Anatomically, the eye includes various tissues that may be beneficially altered by laser surgery. These include: the cornea, the crystalline lens, and the retina. Importantly, a thorough knowledge of the geometry of these ocular elements, and of their geometrical relationship to each other, is essential for successful surgery. All of this, of course, cannot be done by merely an external examination of the eye. With this limitation in mind, one method for imaging the interior of an eye involves optical coherence tomography (OCT) techniques. Fortunately, these techniques are well known to skilled artisans (e.g. See U.S. Pat. No. 6,004,314 which issued to Wei et al. for an invention entitled "Optical Coherence Tomography Assisted Surgical Apparatus"). Specifically, for purposes of the present invention, OCT can be employed to identify an appropriate eye-based reference datum for conduct of the laser surgery. Further, OCT provides a means for visualizing a treatment area inside the eye, while laser surgery is being performed. Although OCT techniques may be preferred, it will be appreciated by the skilled artisan that other imaging techniques might be used for the purposes of the present invention. Specifically, imaging techniques such as confocal microscopy, Scheimpflug principle, or second harmonic generation microscopy, may be employed.

In light of the above, it is an object of the present invention to provide a method and apparatus for directing a surgical laser beam onto tissue in a treatment area of an eye of a patient, wherein control of the laser beam is based on cross-sectional views of the eye obtained by employing OCT techniques. Another object of the present invention is to provide a method and apparatus for directing a surgical laser beam onto tissue in a treatment area of an eye of a patient wherein an eye-based reference datum can be selected that is most appropriate for the particular surgical operation that is to be performed. Still another object of the present invention to provide a method and apparatus for directing a surgical laser beam onto tissue in a treatment area of an eye of a patient that is easy to implement, is relatively simple to manufacture, and is comparatively cost effective.

SUMMARY OF THE INVENTION

In accordance with the present invention, an apparatus and a method are provided for performing ocular surgery. In particular, this surgery is accomplished by directing a laser beam onto tissue in a treatment area of a patient's eye; and it requires identifying a reference datum that is related to the eye. For purposes of the present invention, this reference datum can be either the anterior surface of the cornea, the posterior surface of the cornea, a surface area on the crystalline lens, or the retina. To identify the reference datum, the present invention employs an optical detector that creates images using optical coherence tomography (OCT) techniques. Specifically, the detector is used to create cross-sectional views of the eye that include images of both the reference datum and of the treatment area where the tissue that is to be altered by laser surgery is located.

Along with the optical detector, the apparatus of the present invention includes a beam delivery system. Specifically, the beam delivery system has a laser source for generating the surgical laser beam, and it has appropriate optical elements for directing the laser beam from the laser source to the treatment area. Included in these optical elements is a scanner that is able to move the laser beam in orthogonal x, y and z directions. Also, the delivery system includes a lens for focusing the laser beam to a focal point in the treatment area. As intended for the present invention, the surgical laser beam that is generated by the beam delivery system comprises a sequence of femtosecond pulses having a wavelength that is approximately one thousand nanometers ($\lambda_s$=1,000 nm). Preferably, the apparatus also includes a contact lens that can be placed against the anterior surface of the patient's eye, to stabilize the eye during surgery. Further, the contact lens can also establish an interface at the anterior surface between the eye and the apparatus that may be used as a reference datum.

A computer (i.e. a data processor) is electronically connected to both the beam delivery system and to the optical detector. With these connections, the computer is able to compare the location of desired focal points in the treatment area (based on pre-planned data for the surgery) with actual focal points. Deviations of actual focal points from desired focal points (i.e. error signals) can thus be identified. Using well known closed loop feedback control techniques, the delivery system is then adjusted to nullify or minimize the error signals. Consequently the system can be controlled to have its focal point follow a predetermined path through the treatment area. Alternatively, the system can be operated in an open-loop mode. If so operated, the focal point is moved to follow the predetermined path through the treatment area without any further adjustments. In the open-loop mode, however, it is still important to use the optical detector to establish an appropriate start point for the path of the focal point.

As indicated above, an important aspect of the present invention is its use of the optical detector to generate cross-sectional views of the treatment area. As envisioned for the present invention, such views can be sequentially made in real time. Further, they can be made from different perspectives, based on different cross-section planes through the eye. With these capabilities, the cross-sectional views can be used for control of the system, and they can also provide the operator with a three dimensional visualization of the treatment area. With this capability, it is envisioned that manual control over movements of the focal point in the treatment area is possible for the present invention. When used, manual control may either augment the computer control mentioned above, or provide an alternative to the computer control.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which:

FIG. 1 is a schematic drawing of an apparatus for performing ocular surgery in accordance with the present invention;

FIG. 2 is a top plan view of an eye as would be seen along the line 2-2 in FIG. 1;

FIG. 3 is a cross-section view of an eye as seen along the line 3-3 in FIG. 2; and FIG. 4 is an enlarged cross-section view of the cornea of the eye shown in FIG. 3.

DESCRIPTION OF THE PREFERRED EMBODIMENTS

Referring initially to FIG. 1, an apparatus for performing ocular surgery in accordance with the present invention is shown and is generally designated 10. As shown, the apparatus 10 includes a laser source 12 for generating a surgical laser beam 13. For the present invention, the surgical laser beam 13 preferably includes a sequence of femtosecond pulses having a wavelength of approximately one thousand nanometers ($\lambda_s$=1,000 nm). FIG. 1 also implies that the apparatus 10 includes a scanning unit 14 that will allow the surgical laser beam 13 to be moved in orthogonal x, y and z directions. Relay optics 16 transfer the surgical laser beam 13 in a manner well known in the pertinent art, and a focusing lens 18 is used to focus the surgical laser beam 13 to a focal point 20.

As indicated in FIG. 1, the focal point 20 may be selectively established in the tissue of a patient's eye 22. A contact lens 24 that is mounted on the apparatus 10 by way of connections (not shown) is also shown positioned on the eye 22. Further, FIG. 1 indicates the surgical laser beam 13 will follow along a beam path 26 as it progresses from the laser source 12 to its focal point 20 in the eye 22. For this purpose, turning mirrors 28 and 30 can be employed to establish the beam path 26, as desired.

Still referring to FIG. 1, it will be seen that the apparatus 10 includes an optical detector 32 and a computer (data processor) 34. More specifically, the computer 34 is connected via a line 36 to the optical detector 32, and it is connected to the laser source 12 via a line 38. Together, these components (i.e. laser source 12, optical detector 32, and computer 34) effectively control the apparatus 10 during ocular surgery.

As envisioned for the present invention, and stated above, the optical detector 32 uses optical coherence tomography (OCT) techniques to create cross-section views of the eye 22. Importantly, these views include images of specific anatomical features of the eye 22. Moreover, optical detector 32 creates these views (with images) in a way that allows the images to be used by the computer 34 for control of the laser source 12. To better appreciate this function, refer to FIG. 2.

In FIG. 2, the eye 22 is seen in a top plan view; and it is shown with end-on indications of several reference planes 40, 42 and 44. The present invention envisions these planes 40, 42, and 44 will be generally parallel to the optical axis of the eye 22 and will extend through the eye 22. The planes 40, 42 and 44, however, are only exemplary, and their importance is best appreciated by cross referencing FIG. 2 with FIG. 3. Specifically, FIG. 3 is representative of a cross section view of the eye 22 as seen in the single plane 40. The fact that other cross section views of the eye 22 are possible (i.e. the perspectives of planes 42 and 44), allows OCT images to be collectively considered for a three-dimensional presentation of the interior of the eye 22. On the other hand, an individual image from any particular plane (e.g. plane 40, 42 or 44) will, by itself, provide valuable information for the use and operation of apparatus 10.

With specific reference now to FIG. 3 it will be seen that the cross section view presented (i.e. plane 40) specifically reveals several anatomical features of the eye 22. These include: the anterior surface 46 of the cornea 48, the posterior surface 50 of the cornea 481 the crystalline lens 52, and the retina 54. Further, this cross section view also shows details of the contact lens 24, if used. Thus, the interface between contact lens 24 and the anterior surface 46 of cornea 48 can be identified. At this point it is to be noted that less than an entire cross section view (e.g. as shown in FIG. 3) can be used for the purposes of the present invention. For example, an image emphasizing the cornea 48 or the retina 54 may be needed. Further, it is also to be noted that, particular information from an image (e.g. plane 40) can be substantiated or verified by comparing it with images from other planes (e.g. planes 42 or 44).

For purposes of disclosure, the interface between contact lens 24 and the anterior surface 46 of the cornea 48 is hereafter referred to as a reference datum 56. It must be appreciated, however, that this reference datum 56 is only exemplary. Other anatomical features of the eye 22 can be alternatively used for the same purposes, and perhaps more effectively, depending on the requirements of the particular ocular surgery being performed.

Returning for the moment to FIG. 1, it will be seen there are two functional embodiments of the apparatus 10 that are envisioned for the present invention. The primary difference between the two embodiments is determined by the location where optical detector 32 is coupled onto the beam path 26. For both embodiments this coupling is accomplished where the diagnostic beam, used by the optical detector 32 for OCT imaging, joins the beam path 26 of the surgical laser beam 13.

For a preferred embodiment of the present invention, the diagnostic laser beam (represented by the dashed line 58 in FIG. 1) is coupled onto beam path 26 by a dichroic mirror 60. As shown, the dichroic mirror 60 is positioned downstream from the scanning unit 14. In this case, the diagnostic laser beam 58 does not pass through the scanning unit 14. Accordingly, for this preferred embodiment, the optical detector 32 needs to include its own scanning unit (similar to the scanning unit 14 but not shown).

For an alternate embodiment of the present invention, the diagnostic laser beam (represented by the dotted line 62 in FIG. 1) is coupled onto beam path 26 by a dichroic mirror 64 that is located upstream from the scanning unit 14. In this case, the optical detector 32 can use the same scanning unit 14 that is being used for the surgical laser beam 13. As an operational consideration, the diagnostic laser beam 58, 62 for both embodiments will have a wavelength of approximately one thousand three hundred nanometers ($\lambda_d$=1,300 nm). The implication here is the embodiment wherein the diagnostic laser beam 58 is coupled downstream from the scanning unit 14, may be preferable. This is so in order to avoid the additional refinements that are required for scanning unit 14 and the relay optics 16 when two different wavelengths use the same optical elements.

Operation

In the operation of the apparatus 10 of the present invention, a predetermined path 66 for the focal point 20 of surgical laser beam 13 is established for ocular surgery in a treatment area 68 of the eye 22 (see FIG. 4). An image (e.g. FIG. 3), or a partial image thereof, is made using the optical detector 32. Importantly, the image (partial image) needs to include both the reference datum 66 (only exemplary) and a visualization of the treatment area 68. The focal point 20 of the surgical laser beam 13 can then be directed toward a start point 70 that is selected in the context of the reference datum 56 (cross reference FIG. 3 with FIG. 4).

Open loop control of the focal point 20, as it is moved through the treatment area 68, can be achieved by merely moving the focal point 20 along the predetermined path 66 in accordance with pre-programmed instructions in the computer 34. Whenever an open-loop mode of operation is used, however, it is important that the start point 70 be accurately established, and the path 66 be precisely pre-programmed. This will require that a desired focal point 72 coincide with the start point 70, and that the path 66 be properly oriented in the treatment area 68. As envisioned for the present invention, the coincidence of the desired focal point 72 with the required start point 70 can be accomplished using information from the optical detector 32. Thus, using the start point 70, and a predetermined definition of the path 66, the apparatus 10 can be operated in an open-loop mode to perform the desired ocular surgery. On the other hand, closed loop control may be more appropriate for the particular ocular surgery being performed. In this case, the optical detector 32 is activated to provide continuous updates of cross-section images from the eye 22. As indicated in FIG. 4, information contained in such cross-section images will include position data, relative to the reference datum 56, of both an actual focal point 20' and a desired focal point 72 on the path 66. The positional difference "Δ" between the points 20' and 72 will then represent an error signal that can be used for appropriate adjustments of the apparatus 10. According to well known procedures and techniques (i.e. closed loop feedback control techniques), adjustments to the apparatus 10 can be input from the computer 34 that will either nullify or minimize "Δ" to maintain the focal point 20 on path 66 for a successful completion of the ocular surgery.

While the particular System and Method for Precise Beam Positioning in Ocular Surgery as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

What is claimed is:

1. An apparatus for directing a surgical laser beam to tissue in a treatment area of an eye of a patient during ocular surgery, the apparatus comprising:
   a surgical laser source providing a surgical laser beam;
   a beam delivery system for guiding the surgical laser beam along a beam path to a desired focal point in the treatment area;
   an optical detector for creating a planar image of eye tissue wherein the planar image includes visualizations of a selected reference datum and the treatment area and wherein the reference datum is related to an anatomical feature of the eye;
   a computer means, connected to the beam delivery system and to the optical detector, for using the planar image to position the focal point in the treatment area relative to the reference datum, and to guide the beam during surgery;
   a means for sequentially creating a plurality of images with the optical detector;
   a means for continuously monitoring the reference datum with the computer;
   a means for using the reference datum to determine a delta for each image, wherein the delta is a distance between an actual position of the focal point and the position of the desired focal point; and
   a means in the beam delivery system for maintaining the delta at a substantial null.

2. An apparatus as recited in claim 1 wherein the surgical laser beam comprises a sequence of femtosecond pulses.

3. An apparatus as recited in claim 1 further comprising a contact device mounted on the beam delivery system for engagement with the eye to establish the reference datum.

4. An apparatus as recited in claim 3 wherein the contact device is a contact lens and the reference datum is an interface between an external surface of the eye and the contact lens.

5. An apparatus as recited in claim 1 wherein the reference datum is selected from a group consisting of an anterior surface of a cornea, a posterior surface of a cornea, a boundary of a crystalline lens, and a fundus of an eye.

6. An apparatus as recited in claim 1 wherein the optical detector employs techniques selected from a group comprising optical coherence tomography (OCT), confocal microscopy, Scheimpflug principle and second harmonic generation microscopy.

7. An apparatus as recited in claim 6 wherein a portion of the beam path is in the plane of the image.

8. An apparatus as recited in claim 1 wherein the beam delivery system, in sequence along the beam path, comprises:
   a scanning unit for moving the focal point of the surgical laser beam in orthogonal x, y and z directions; and
   a focusing lens for establishing the focal point.

9. An apparatus as recited in claim 8 wherein the optical detector includes a secondary scanning unit and is positioned to couple a diagnostic beam onto the beam path of the surgical laser beam at a point between the scanning unit and the focusing lens.

10. An apparatus as recited in claim 9 wherein the wavelength of the surgical laser beam is approximately one thousand nanometers ($\lambda_s$=1,000 nm).

11. An apparatus for directing a surgical laser beam to a treatment area of a substantially transparent material, wherein the transparent material includes a first portion having a first refractive index and a second portion having a second refractive index to establish an interface therebetween, the apparatus comprising:

a surgical laser source providing a surgical laser beam;

a means for guiding the surgical laser beam along a beam path to a desired focal point in the treatment area;

an optical coherence tomography (OCT) detector for creating a planar image of the material, wherein the planar image includes visualizations of a selected reference datum and the treatment area and wherein the reference datum is related to the interface;

a computer means for positioning the focal point in the treatment area relative to the reference datum in the image, and for guiding the beam during surgery;

a means for sequentially creating a plurality of images with the optical detector;

a means for continuously monitoring the reference datum with the computer;

a means for using the reference datum to determine a delta for each image, wherein the delta is a distance between an actual position of the focal point and the position of the desired focal point; and a means for maintaining the delta at a substantial null.

12. An apparatus as recited in claim 11 wherein the surgical laser generating means comprises:

a primary scanning unit for moving the focal point of the surgical laser beam in orthogonal x, y and z directions; and a focusing lens for establishing the focal point.

13. An apparatus as recited in claim 12 further comprising a secondary scanning unit, wherein the secondary scanning unit is positioned to couple a diagnostic beam onto the beam path of the surgical laser beam at a point between the primary scanning unit and the focusing lens.

14. An apparatus as recited in claim 11 wherein the transparent material is in an eye and the apparatus further comprises a contact lens mounted on the beam delivery system for engagement with the eye to establish the reference datum, and wherein the reference datum is an interface between an external surface of the eye and the contact lens.

15. An apparatus as recited in claim 11 wherein the planar image is a cross-sectional image.

* * * * *